United States Patent [19]

Schroeder

[11] Patent Number: 4,845,218

[45] Date of Patent: Jul. 4, 1989

[54] PREPARATION OF N-METHYLPIPERAZINE

[75] Inventor: Wolfgang Schroeder, Bad Duerkheim, Fed. Rep. of Germany

[73] Assignee: BASF Aktiengesellschaft, Ludwigshafen, Fed. Rep. of Germany

[21] Appl. No.: 15,238

[22] Filed: Feb. 17, 1987

[30] Foreign Application Priority Data

Feb. 18, 1986 [DE] Fed. Rep. of Germany ....... 3605005

[51] Int. Cl.$^4$ .......................................... C07D 295/02
[52] U.S. Cl. .................................................... 544/404
[58] Field of Search ............................... 544/358, 404

[56] References Cited

U.S. PATENT DOCUMENTS

| | | | |
|---|---|---|---|
| 2,525,223 | 10/1950 | Howard | 544/358 |
| 2,911,407 | 11/1959 | Langdon et al. | 544/358 |
| 3,037,023 | 5/1962 | Moss et al. | 544/358 |
| 3,112,318 | 11/1963 | Lemon et al. | 544/358 |
| 3,948,900 | 4/1976 | Moss | 544/358 |
| 4,009,124 | 2/1977 | Laurer et al. | 252/443 |

FOREIGN PATENT DOCUMENTS

| | | |
|---|---|---|
| 137478 | 10/1984 | European Pat. Off. |
| 1953263 | 2/1972 | Fed. Rep. of Germany |
| 2531060 | 2/1976 | Fed. Rep. of Germany |
| 2445303 | 4/1976 | Fed. Rep. of Germany |
| 3125662 | 1/1983 | Fed. Rep. of Germany |
| 7605640 | 12/1976 | Netherlands |
| 902570 | 8/1962 | United Kingdom |
| 1319495 | 6/1973 | United Kingdom |
| 1491390 | 11/1977 | United Kingdom |

OTHER PUBLICATIONS

Ondetti, Mercaptoacyl Derivatives of Keto Substituted Proline and Pipecolic Acid, CA 96-7075u, equiv. JP '261.

Schroeder et al, Catalyst and Method for Producing Cyclic Imines. CA98-198257d, eq. DE'662.

Schroeder et al., N-Methylated Cyclic Imines, CA 103-215303g, equiv. DE '182.

Primary Examiner—Anton H. Sutto
Assistant Examiner—Cecilia Shen
Attorney, Agent, or Firm—Keil & Weinkauf

[57] ABSTRACT

A process for the preparation of N-methylpiperazine from diethanolamine and methylamine, wherein the reaction is carried out at elevated temperature and superatmospheric pressure in the presence of hydrogen over a metal-containing catalyst.

5 Claims, No Drawings

PREPARATION OF N-METHYLPIPERAZINE

The present invention relates to a process for the preparation of N-methylpiperazine.

N-Methylpiperazine is an important intermediate in the synthesis of dyes, drugs and crop protection agents.

The prior art processes for the preparation of N-methylpiperazine may be divided into two groups.

One type of process comprises the methylation of piperazine. Such a process is described in, for example, DE-B-2 531 060.

A disadvantage of the processes which use piperazine as the starting material is that piperazine is not a deliberately produced material and instead is generally formed as a by-product of other syntheses. Accordingly, piperazine is not always available in the desired amount and at the desired price.

This difficulty has resulted in the development of a second general type of synthesis, based on a cyclization reaction.

For example, NL-A-7 605 640 teaches reacting N-methyldiethanolamine with ammonia, with the aid of dehydrating agents.

In the process of JP-A-81/133 261, diethanolamine is reacted with monomethylamine with the aid of heteropolyacids.

It is true that some of the prior art processes start from inexpensive materials, but they have the disadvantage of low yields. For example, NL-A-7 605 640 reports a selectivity of 13%. This makes the synthesis of N-methylpiperazine completely uneconomical.

The literature also describes other methods of synthesis for the preparation of N-methylpiperazine, but they are only in the nature of laboratory methods. One example is the reaction of N-benzoylpiperazine with a mixture of formic acid and formaldehyde, followed by hydrolysis, cf. SU-A-0146314.

It is the object of the present invention to provide a process for the preparation of N-methylpiperazine which starts from inexpensive and universally available materials, can readily be scaled up to industrial operation, giving high yields, and does not suffer from the disadvantages of the prior art processes.

We have found that this object is achieved by a process for the preparation of N-methylpiperazine from diethanolamine and methylamine, wherein the reaction is carried out at elevated temperature and superatmospheric pressure in the presence of hydrogen over a metal-containing catalyst.

In a preferred embodiment, the reaction is carried out substantially in the liquid phase. This means that a liquid phase is present in the reactor, and this phase may be pervaded by, for example, bubbles of gaseous hydrogen. The liquid phase may be continuous or discontinuous, the latter being preferred.

The preferred temperature range is from 180° to 230° C., especially from 190° to 220° C. At lower temperatures the proportion of non-volatile by-products increases and at higher temperatures the proportion of other by-products increases. Piperazine is in every case formed in only insignificant amounts, of the order of 1%. The molar ratio of diethanolamine to monomethylamine is in general from 1:5 to 1:20. With decreasing excess of monomethylamine, the proportion of non-volatile by-products increases. If the excess monomethylamine increases above the upper limit, there is hardly any further reduction in the proportion of non-volatile by-products but the economics of the process are increasingly adversely affected.

The preferred pressure ranges from 50 to 300 bar, especially from 100 to 250 bar. The pressure in excess of the vapor pressure of the materials involved is provided by hydrogen. The presence of hydrogen assists the selectivity and activity of the catalyst.

Suitable metal-containing catalysts are, in particular, supported metal-containing catalysts. The term "metal-containing" means that the catalyst contains a metal or metal salt (which term includes metal oxides) as the active component. As examples of suitable metal containing catalysts there may be mentioned:

extrudates of active alumina impregnated with copper nitrate solution, which after drying and calcining contain about 20% by weight of CuO, extrudates of active alumina impregnated with a mixed solution of nitrates of copper, nickel and cobalt, which, after drying and calcining, contain about 10% by weight of NiO, 10% by weight of CoO and 5% by weight of CuO, particles produced by coprecipitation from a mixed solution and containing, after drying and calcining, about 30% by weight of CuO, 10% by weight of NiO and 60% by weight of $Al_2O_3$ and particles produced from a mixed solution by coprecipitation and containing, after drying and calcining, about 45% by weight of CuO and 55% by weight of $Al_2O_3$.

Such catalysts are described, for example, in DE-A-19 53 263, DE-A-24 45 303 and DE-A-31 25 662.

Particularly preferred catalysts are those wherein the active component is principally copper. Such catalysts may for example contain from 10 to 60% of copper in the form of metallic copper or copper ions (including oxides). Further possible components of the catalyst are chromium, manganese, cobalt, nickel and silver.

A particularly preferred supported catalyst contains about 35 to 55% by weight of copper, based on total weight of catalyst. Aluminum oxide, for example gamma-aluminum oxide, is a particularly suitable carrier. The catalyst may be in various forms, for example in the form of cylindrical tablets, or of rings and the like. Particularly suitable dimensions are a height and diameter each of about 2-7 mm.

Apparatuses known per se, for example tubular reactors or shaft reactors are suitable for carrying out the reaction and for setting up the conditions according to the invention. In such a reactor, the catalyst is present as a fixed bed of tablets or extrudates. The feed mixture, which under the reaction conditions is predominantly liquid, is preheated to the reaction temperature and then preferably introduced at the top of the reactor, from where it flows down through the catalyst bed to constitute a trickle phase. Because of the low heat of reaction, the reaction is virtually isothermal. As the crude reaction product cools, a small amount of hydrogen, and the methylamine, dissolve therein. On releasing the pressure, the entire dissolved entrained hydrogen and a major portion of the methylamine escape. Normally, the hydrogen is removed as off-gas while the methylamine is recovered and recycled to the reaction. The methylamine still present in the reaction mixture after the pressure release is treated similarly.

Normally, the diethanolamine is completely converted after only one pass through the reactor. Alongside the main product, a few per cent each of various low-boiling materials are formed, these materials being essentially diethanolamine cleavage products and reaction products thereof with methylamine. Furthermore, the reaction mixture contains a few percent of high-boiling materials, of which some are not heat-stable.

To work up the reaction mixture, the unconverted methylamine is removed and recovered. This may be carried out by conventional methods. The small amounts of high-boiling by-products formed are also removed in a conventional manner. The final purification of the N-methylpiperazine may be carried out particularly advantageously by distillation. In this way, the desired product is obtained in a purity of more than 99.5% and in yields which may be as much as over 70%.

The process according to the invention may be carried out continuously or batchwise, the former being particularly advantageous.

The Example which follows illustrates the invention.

EXAMPLE 4 liters of catalyst were introduced into a reactor of 350 cm length and 4.3 cm internal diameter. The catalyst contained 45% by weight of copper and 55% by weight of aluminum oxide and had been molded into cylindrical tablets of height=diameter=4 mm. External heating ensured a constant temperature in the reactor. The reactor comprised two stock vessels for diethanolamine (I) and for monomethylamine (II), from which the predetermined amounts of 0.4 liter/h of (I) and 1.6 liters/h of (II) were pumped continuously into the reactor. The reactor was preceded by a preheater in which the feed was heated to 200° C.

The pressure in the reactor system was set to 250 bar with pressurized hydrogen.

The feed mixture flowed downward as a trickle phase through the catalyst bed. After it had left the reactor, it was cooled to 20° C. and the product mixture was collected in a high pressure separator. From there, it was released to atmospheric pressure in a single step, after which the product mixture still contained 15% by weight of monomethylamine. Leaving out of account the water formed in the reaction, and the dissolved methylamine, the product mixture consisted of 71% by weight of monomethylpiperazine, 1% by weight of piperazine, 23% by weight of other by-products and 5% by weight of evaporation residue.

This mixture was worked up by two-stage batchwise distillation. In the first stage, first the methylamine and then all the remaining material were separated from the non-volatile residue. In the second stage, this main fraction was subjected to fractional distillation under atmospheric pressure. The methylpiperazine passed over at a boiling point of 137° C. measured at the top of the distillation column and w obtained in a purity of 99.8%, determined by gas-chromatographic analysis, using 4 m carbowax.

I claim:

1. A process for the preparation of N-methylpiperazine from diethanolamine and methylamine which comprises: reacting diethanolamine with methylamine at, from the beginning of the reaction, an elevated temperature of 180° to 230° C. and a superatmospheric pressure of 50 to 300 bar in the presence of hydrogen, over a metal-containing catalyst.

2. The process of claim 1, wherein the reaction is carried out in a substantially liquid phase.

3. The process of claim 1, wherein an excess of methylamine is employed.

4. The process of claim 1, wherein a copper-containing catalyst is employed.

5. The process of claim 1, wherein a molar ratio of diethanolamine to monomethylamine of from 1:5 to 1:20 is employed.

* * * * *